United States Patent
Van Vlem (10) Patent No.: US 12,323,771 B2
(45) Date of Patent: Jun. 3, 2025

(54) SYSTEMS FOR ACCOMMODATING SEPARATION OF BODY PARTS IN AUDITORY PROSTHESES

(71) Applicant: Cochlear Limited, Macquarie University (AU)

(72) Inventor: Jürgen Van Vlem, Mechelen (BE)

(73) Assignee: Cochlear Limited, Macquarie University (AU)

( * ) Notice: Subject to any disclaimer, the term of this patent is extended or adjusted under 35 U.S.C. 154(b) by 1301 days.

(21) Appl. No.: 17/017,858

(22) Filed: Sep. 11, 2020

(65) Prior Publication Data

US 2021/0051426 A1 Feb. 18, 2021

Related U.S. Application Data

(63) Continuation of application No. 14/832,950, filed on Aug. 21, 2015, now Pat. No. 10,805,744.

(60) Provisional application No. 62/043,027, filed on Aug. 28, 2014.

(51) Int. Cl.
*H04R 25/00* (2006.01)
*A61N 1/375* (2006.01)

(52) U.S. Cl.
CPC ............ *H04R 25/606* (2013.01); *A61N 1/375* (2013.01); *H04R 25/658* (2013.01)

(58) Field of Classification Search
CPC .... H04R 25/60; H04R 25/604; H04R 25/606; H04R 25/658; A61N 1/36038; A61N 2225/67
See application file for complete search history.

(56) References Cited

U.S. PATENT DOCUMENTS

| | | | |
|---|---|---|---|
| 5,057,111 A | 10/1991 | Park | |
| 7,204,800 B2 | 4/2007 | Easter | |
| 8,075,600 B2 | 12/2011 | Schlapfer | |
| 10,805,744 B2 | 10/2020 | Van Vlem | |
| 2002/0035308 A1 | 3/2002 | Brillhart | |
| 2003/0065245 A1* | 4/2003 | Easter | H04R 25/606 600/25 |
| 2008/0058927 A1* | 3/2008 | Brosnahan | A61F 2/18 623/10 |

(Continued)

FOREIGN PATENT DOCUMENTS

| | | | | |
|---|---|---|---|---|
| DE | 20229004715 | * | 7/2009 | ............... A61F 2/18 |
| KR | 100859979 B1 | | 9/2008 | |
| WO | WO2013023693 | * | 2/2013 | ........... H04R 25/606 |

OTHER PUBLICATIONS

DSM Biomedical, Inc., "Bionate thermoplastic polycarbonate polyurethane (PCU)" product sheet, 2012, 4 pgs.

(Continued)

*Primary Examiner* — Carrie R Dorna
(74) *Attorney, Agent, or Firm* — Edell, Shapiro & Finnan, LLC (57) ABSTRACT

An auditory prosthesis includes a fixation system manufactured in whole or in part from a deformable material, such as a viscoelastic material. The viscoelastic material responds viscously to loads applied over an extended period of time. Thus, the material is able to accommodate growth of a recipient's anatomy without becoming disconnected or misaligned from any attachment points. This allows the device to accommodate growth of a recipient over time.

20 Claims, 11 Drawing Sheets

(56) References Cited

U.S. PATENT DOCUMENTS

| | | | | |
|---|---|---|---|---|
| 2009/0306458 A1* | 12/2009 | Parker | .................. | H04R 25/606 |
| | | | | 600/25 |
| 2011/0106254 A1* | 5/2011 | Abel | ........................ | A61F 2/18 |
| | | | | 623/16.11 |
| 2011/0295053 A1 | 12/2011 | Ball | | |
| 2012/0078368 A1* | 3/2012 | Lenarz | ................. | H04R 25/606 |
| | | | | 623/10 |
| 2012/0239113 A1* | 9/2012 | Vermeiren | ........... | H04R 25/606 |
| | | | | 607/57 |
| 2013/0225912 A1 | 8/2013 | Leigh | | |

OTHER PUBLICATIONS

Montgomery T. Shaw et al. "Introduction to Polymer Viscoelasticity, Third Edition" Aug. 17, 2005 (Year: 2005).

PCT International Search Report and Written Opinion in International Application PCT/IB2015/001914, mailed Jan. 29, 2016, 15 pgs.

Viscoelasticity. (1992). In C. G. Morris (Ed.), Academic Press Dictionary of Science and Technology (4th ed.). Oxford, UK: Elsevier Science & Technology. Retrieved from https://search.credoreference.com/content/entry/apdst/viscoelasticity/0?institutionld=7 43 (Year: 1992).

* cited by examiner

SYSTEMS FOR ACCOMMODATING SEPARATION OF BODY PARTS IN AUDITORY PROSTHESES

BACKGROUND

A direct acoustic cochlear implant is fixed at two locations. At a first end, the device is fixed to a skull surface by a fixation system and a number of bone screws. At a second end, it is attached to the cochlea by means of a stapes prosthesis or preloaded to the ossicular chain. The direct acoustic cochlear implant includes an actuator, a coupling rod, an artificial incus, and/or a drive pin, to deliver stimulation directly to the cochlea.

As the skull of a juvenile grows, the distance between the attachment point at the skull surface and the attachment point at the inner ear or middle ear structures increase. This could result in a dislocation or misalignment of the connections. Most likely, the connection to the inner ear or middle ear structures will loosen because that connection is weaker than the connection to the skull surface. A dislocated or misaligned connection to the inner ear or middle ear results in loss of therapy efficiency or efficacy. Therefore, direct acoustic cochlear implants are contra-indicated for recipients that do not have full-grown anatomy, e.g. skull anatomy. This can exclude pediatrics, teens, and other potential recipients whose anatomy is still growing, from the benefits of such an acoustic implant.

SUMMARY

In an auditory prosthesis, a part of a fixation system (e.g., a part that holds an actuator) is manufactured from a deformable material, such as a viscoelastic material. The viscoelastic material responds elastically to loads that are applied in a short time, but responds viscously when loads are applied over an extended period of time. Thus, the material is able to accommodate growth of a recipient's anatomy without becoming disconnected or misaligned from any attachment points. This allows the device to accommodate growth of a recipient over time, while still allowing the fixation system to respond in a conventional manner to loads due to, for example, inertia.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1A:
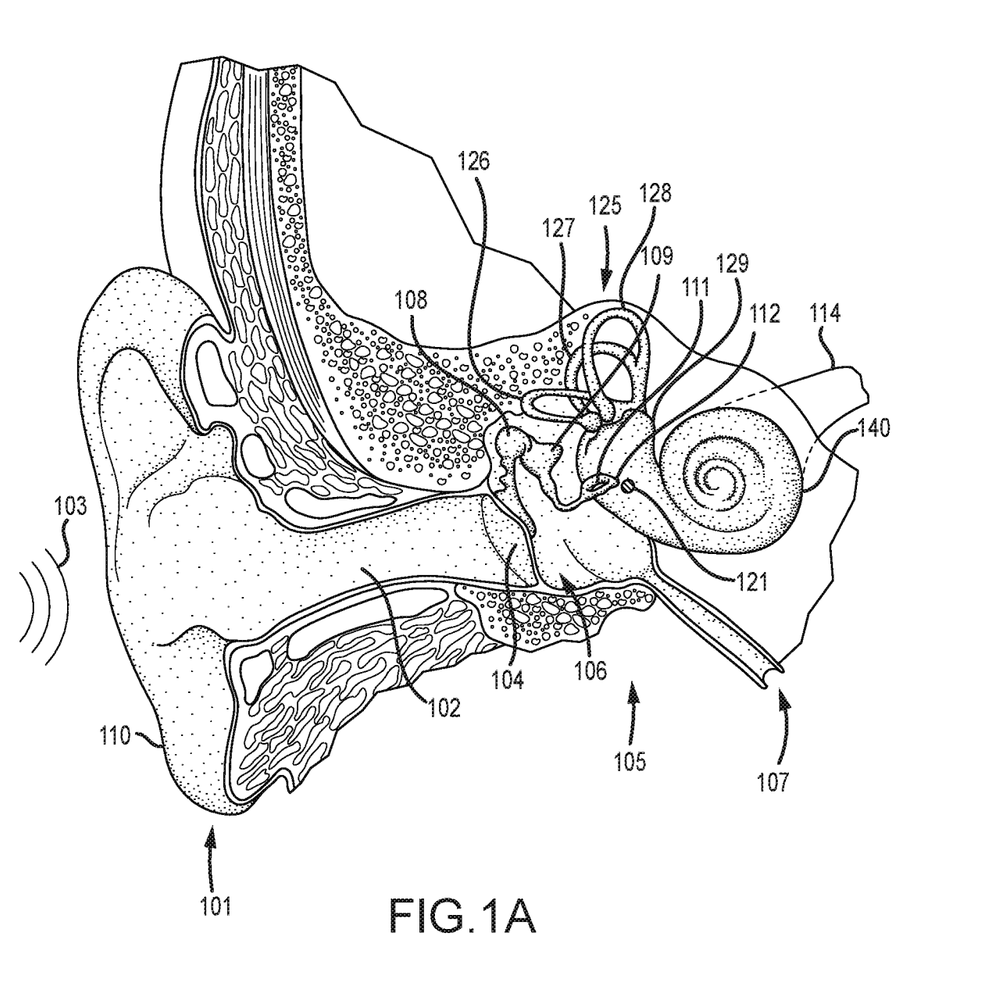
FIG. 1A is a partial view of a fully-functional ear of a recipient.

FIG. 1A is perspective view of fully functional ear of a recipient. The recipient has an outer ear 101, a middle ear 105 and an inner ear 107. Components of outer ear 101, middle ear 105 and inner ear 107 are described below. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Figure 1B:
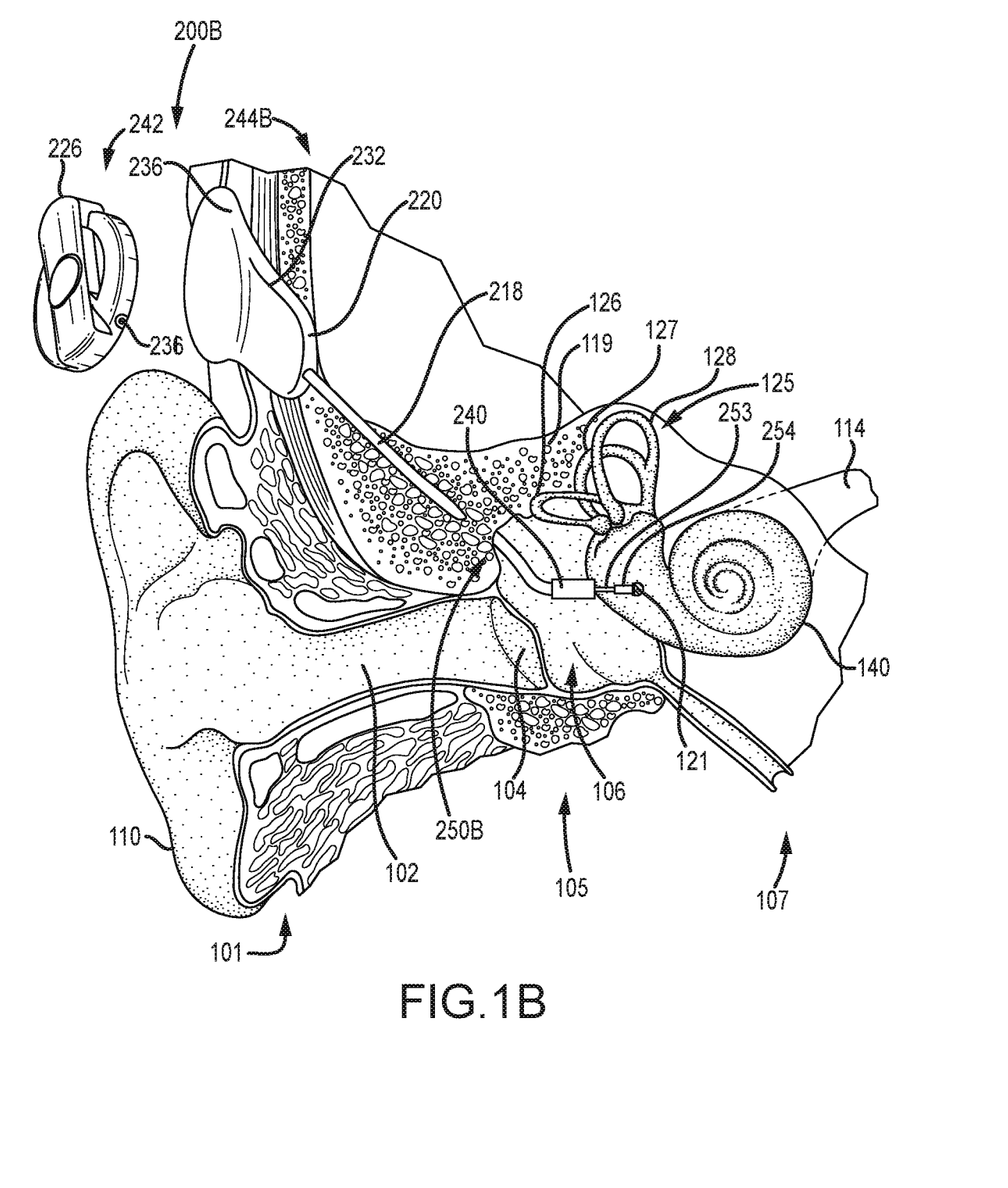
FIG. 1B is a partial view of a direct acoustic stimulator worn on a recipient.

FIG. 1B is a perspective view of a direct acoustic stimulator 200B, comprising an external component 242 which is directly or indirectly attached to the body of the recipient, and internal component 244B which is implanted in the recipient. Elements of the ear are depicted and described above in FIG. 1A and are thus necessarily not described further. External component 242 typically comprises one or more sound input elements, such as microphones 224, sound processing unit 226, a power source (not shown), and an external transmitter unit (also not shown). The internal component 244B comprises internal receiver unit 232, stimulator unit 220, and stimulation arrangement 250B. Stimulation arrangement 250B is implanted in middle ear 105. For ease of illustration, ossicles 106 have been omitted from FIG. 1B. However, it should be appreciated that stimulation arrangement 250B can be implanted without disturbing ossicles 106.

Stimulation arrangement 250B comprises actuator 240, stapes prosthesis 254 and coupling element 253 connecting the actuator 240 to the stapes prosthesis 254. A bracket (depicted and described below with regard to FIGS. 2 and 3) maintains a position of the actuator 240. In this example, stimulation arrangement 250B is implanted and/or configured such that a portion of stapes prosthesis 254 abuts round window 121. It should be appreciated that stimulation arrangement 250B can alternatively be implanted such that stapes prosthesis 254 abuts an opening in horizontal semicircular canal 126, in posterior semicircular canal 127 or in superior semicircular canal 128.

A sound signal is received by one or more microphones 224, processed by sound processing unit 226, and transmitted as encoded data signals to internal receiver 232. Based on these received signals, stimulator unit 220 generates drive signals that cause actuation of actuator 240. This actuation is transferred to stapes prosthesis 254 such that a wave of fluid motion is generated in the perilymph in scala tympani. Such fluid motion, in turn, activates the hair cells of the organ of Corti. Activation of the hair cells causes appropriate nerve impulses to be generated and transferred through the spiral ganglion cells (not shown) and auditory nerve 114 to the brain (also not shown) where they are perceived as sound.

FIG. 1B provides an illustrative example of a direct acoustic stimulator system, more specifically, a direct acoustic cochlear stimulator. A middle ear mechanical stimulation device can be configured in a similar manner, with the exception that instead of the actuator 240 being coupled to the inner ear of the recipient, the actuator is coupled to a middle ear structure of the recipient. For example, the actuator can stimulate the middle ear by direct mechanical coupling via a coupling element (e.g., similar to coupling element 253) to ossicles 106 or to incus 109, which are depicted in FIG. 1A. The technologies disclosed herein can be used in conjunction with both of these types of auditory prostheses, depending on recipient need. Additionally, the technologies can be used in other medical implant applications where accommodation of growth or positional changes to bone or connective or other tissue are desired. For clarity, however, the technologies will be described below in the context of direct acoustic cochlear implants. The middle ear mechanical stimulation device or the direct acoustic cochlear implant can each be referred to generally as a direct acoustic stimulator.

Figure 2A:
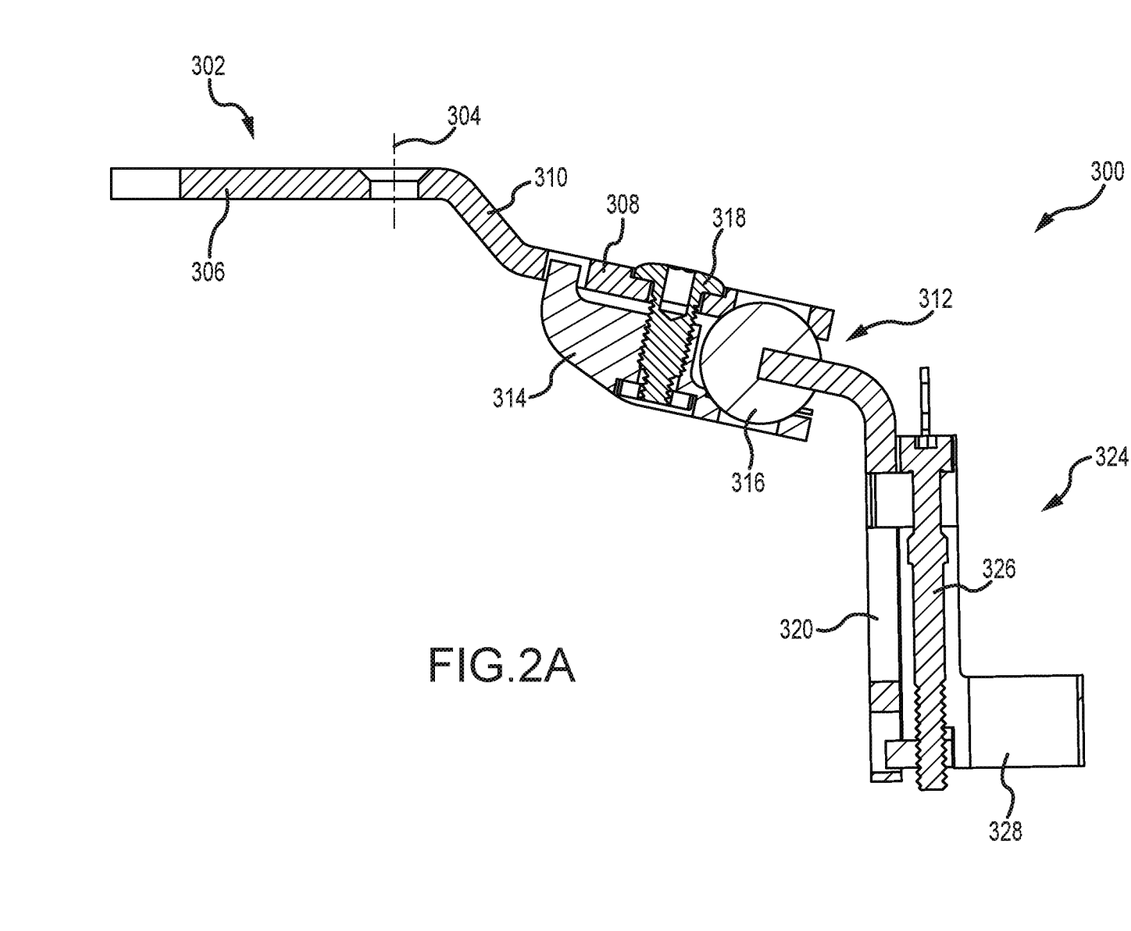
FIGS. 2A and 2B are side sectional and top perspective views, respectively, of a direct acoustic stimulator bracket for use in a direct acoustic stimulator.
Figure 2B:
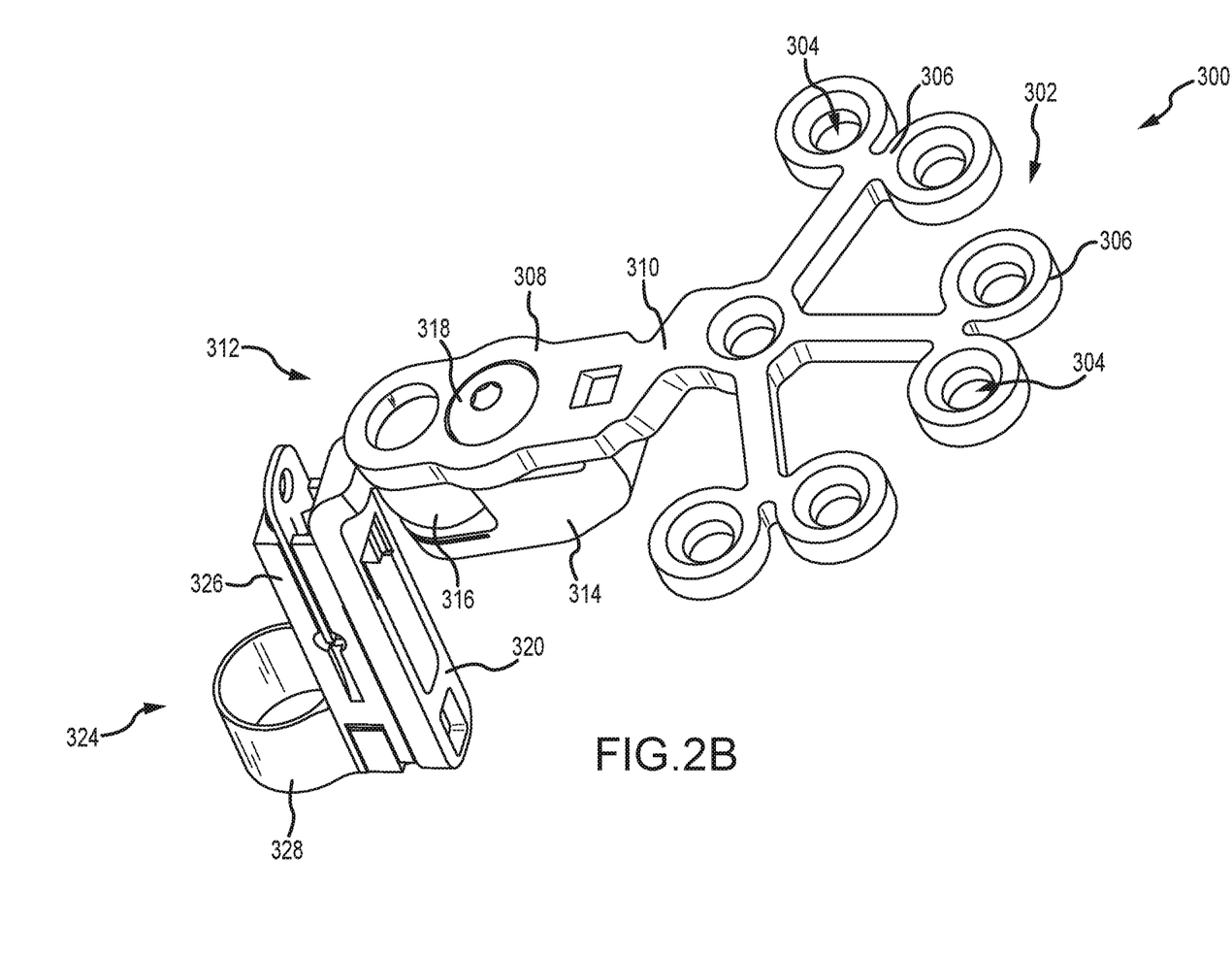

FIGS. 2A and 2B are side sectional and top perspective views, respectively, of a direct acoustic stimulator bracket 300 for use in a direct acoustic stimulator. FIGS. 2A and 2B are described simultaneously. The direct acoustic stimulator bracket 300 includes a number of subparts or components that aid in securing an actuator to a recipient such that stimulation can be delivered to the recipient's internal ear structure. A fixation element 302 defines a number of openings 304 therein for receipt of bone screws. The fixation element 302 includes a bone plate 306 that defines the openings 304. The bone plate 306 is connected to a clamp plate 308 via a transition 310. Each portion of the fixation element 302, the bone plate 306, clamp plate 308, and transition 310 can be configured as required or desired for a particular application. In general, the fixation element 302 is sized and configured so as to be secured to the skull of the recipient. An adjustable joint 312 is used to further align an acoustic actuator (not shown) with the desired internal ear anatomy, as described in further detail below. The adjustable joint 312 includes a ball clamp 314 that, along with the clamp plate 308, defines a socket and secures a ball 316. A position of the ball 316 can be set utilizing a clamp screw 318. A ball plate 320 extends from the ball 316 and enables positioning of an actuator assembly 322 that includes an actuator plate 326 and an actuator clamp 328 for retaining the acoustic actuator.

Figure 3:
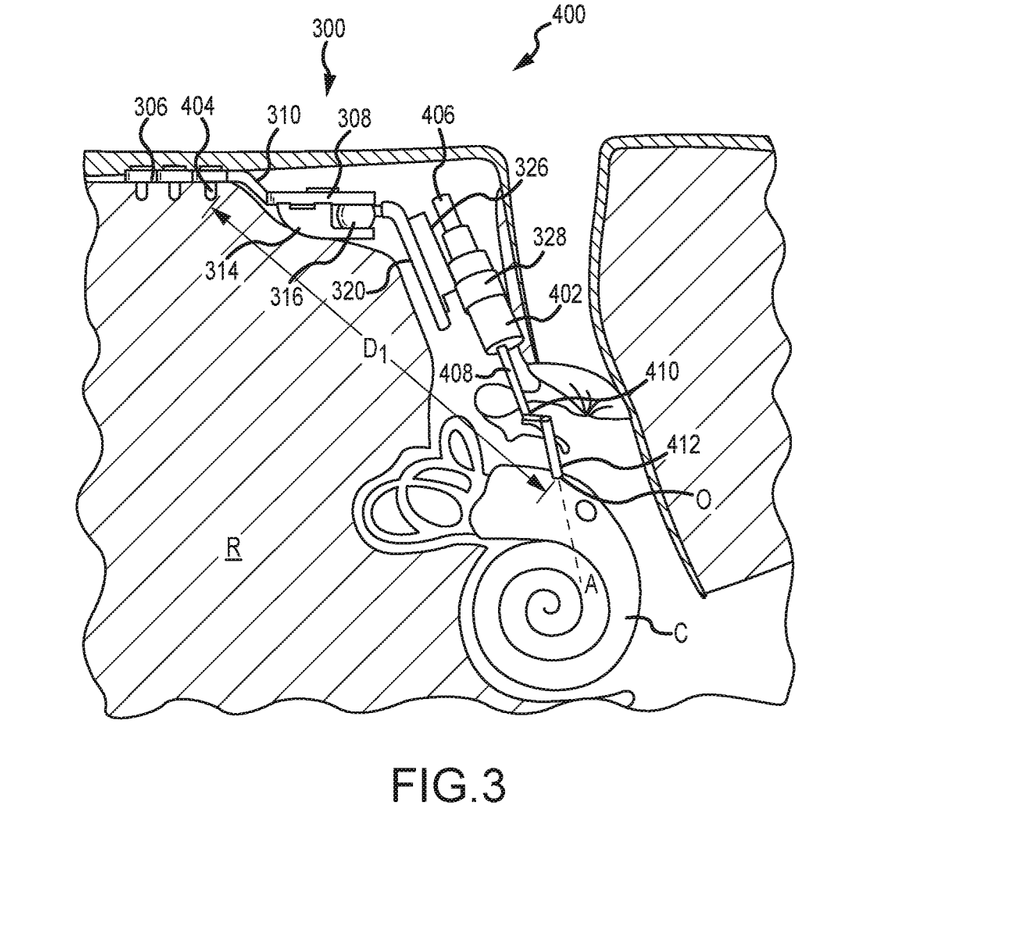
FIG. 3 is a partial view of a direct acoustic stimulator implanted in a recipient.

FIG. 3 is partial view of a direct acoustic stimulator 400 implanted in a recipient R. The direct acoustic stimulator 400 includes the bracket 300 as described above that secures an actuator 402, via the actuator ring 328. Certain subparts or components of the bracket 300 are described above with regard to FIG. 2 and thus are not described further. The bone plate 306 is secured to a skull of the recipient R via a number of bone screws 404. The actuator 402 is in communication with the sound processing components described above via a wire 406. In this embodiment, the actuator 402 drives a coupling or actuation rod 408. The coupling rod 408 can be connected to a mounting structure 410 that is connected to an actuating prosthesis or attachment element 412. In certain embodiments, attachment element 412 is attached to the mounting structure 410 by a wire or rod that is wound around and crimped to the mounting structure 410. The attachment element 412 penetrates an opening O in the cochlea C, and is secured thereto by the fluid tension displayed by fluid within the cochlea. Thus, in this embodiment, the attachment element 412 is a stapes prosthesis and is attached to the inner ear of the recipient. In the illustrated embodiment the stapes prosthesis passes through stapes footplate into the cochlea. In other embodiments, the acoustic stimulator can be connected to a portion of the middle ear, for example, the stapes or ossicle. When connected to the middle ear, the attachment element 412 is an ossicular chain prosthesis. Depending on the size of the opening O in the cochlea C, scar tissue can form around the attachment element 412, further securing the attachment element 412 to the cochlea C. The mounting structure 410 and attachment element 412 transmit movement of the coupling rod 408 to the fluid within the cochlea C, along an axis A. By orienting the attachment element 412 along axis A during implantation, the forces associated with movement of the cochlear rod 408 are directed into the cochlea C to ensure efficient therapy. A distance $D_1$ between an anchor point (e.g., the screw 404, bone plate 306, etc.) and an attachment point (e.g., the interface between the attachment element 412 and the opening O) is also depicted.

Figure 4:
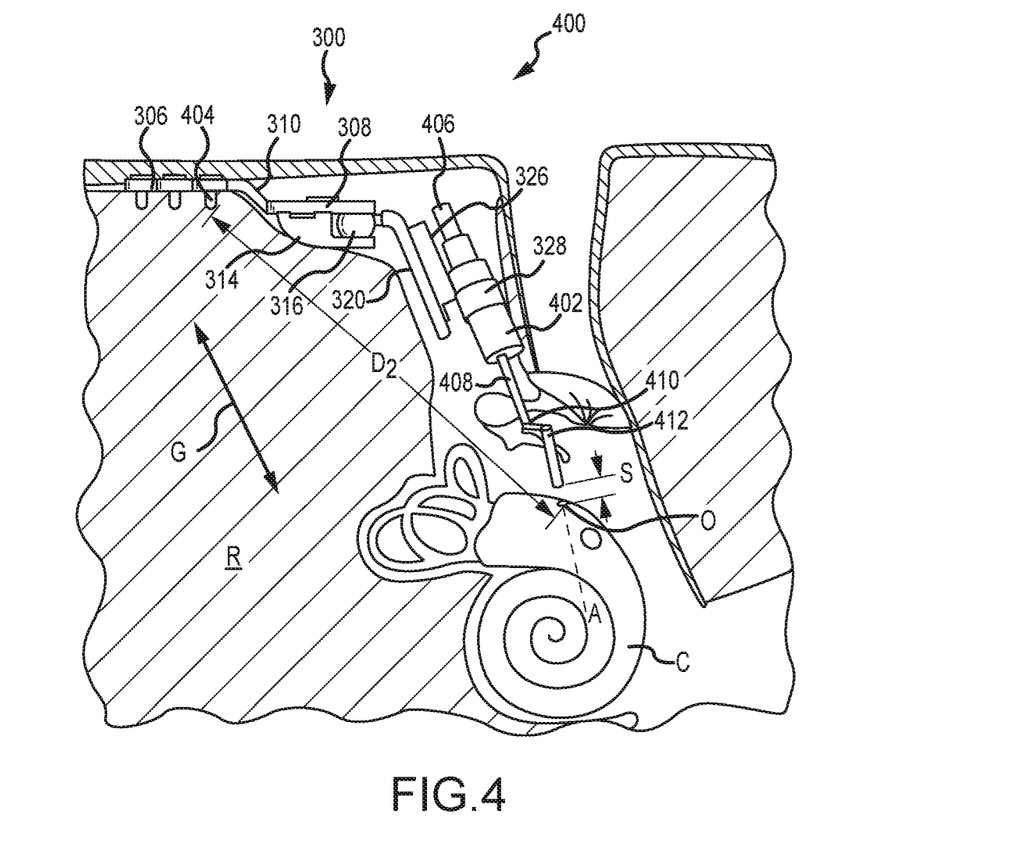
FIG. 4 is a partial view of a direct acoustic stimulator that has disconnected from attachment with an internal ear structure of a recipient.

FIG. 4 is partial view of the direct acoustic stimulator 400 that has disconnected from attachment with an internal ear structure of a recipient R. Certain components depicted in FIG. 4 are described above in FIG. 2 or 3 and are not necessarily described further. As the skull grows G, the distance between the anchor point and the attachment point can increase to a distance $D_2$. As depicted, this can cause the attachment element 412 to separate S from the opening O, due to the fairly weak retention force holding the attachment element 412 in the opening O. This can cause a loss or reduction in therapy efficiency. Depending on the strength of the bone screws 404 and force created by the new distance $D_2$, the bone plate 306 could instead separate. Even if both the bone plate 306 and attachment element 412 remain connected to their respective attachment points, the difference between the original distance $D_1$ and the new distance $D_2$ can cause a bending or twisting of any or all of the coupling rod 408, mounting structure 410, and attachment element 412. This can cause a misalignment of the attachment element 412 relative to the axis A, which can alter the forces applied by actuator 402. This, too, can reduce therapy efficiency. For at least these reasons, aspects of the technology incorporate a deformable material into one or more components of the direct acoustic stimulator 400.

Different types of deformable materials can be utilized in the mounting systems described herein. In certain embodiments, a deformable material is a material that can flex, stretch, or bend from an original position to a deformed position and then return substantially to its original position. In other embodiments, deformable materials can deform from an original position to a deformed position and still maintain functionality. That is, the material can deform to a deformed position without being susceptible to failure. Acceptable deformable materials include viscoelastic materials, such as thermoplastic polycarbonate polyurethane (PCU), such as the Bionate PCU family of materials manufactured by DSM Biomedical Inc., of Berkeley Calif. Other acceptable viscoelastic materials include ultra-high-molecular-weight polyethelene (UHMWPE).

Figure 5A:
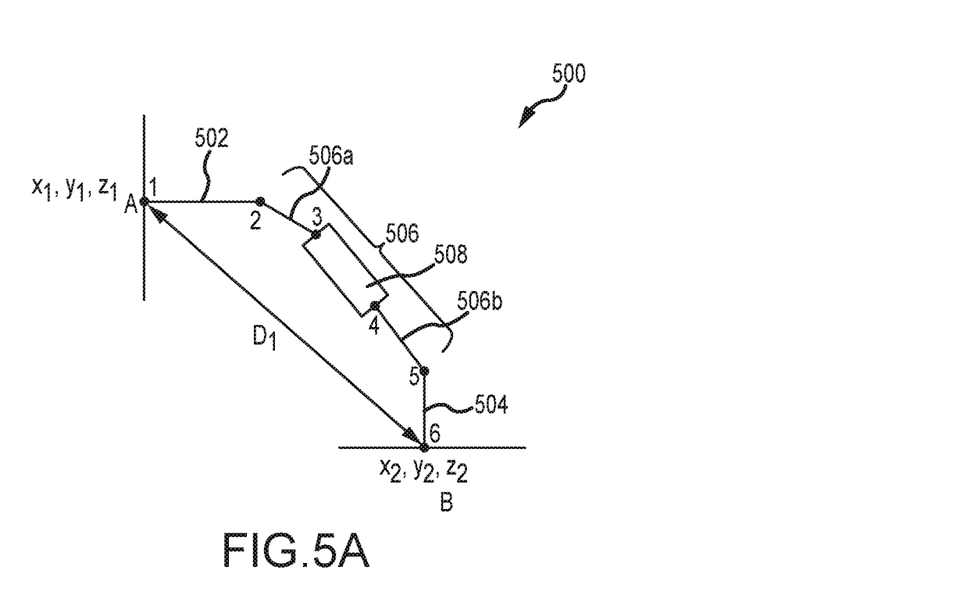
FIGS. 5A-5C depict schematic views of deformable mounting systems for use in direct acoustic stimulators.
Figure 5B:
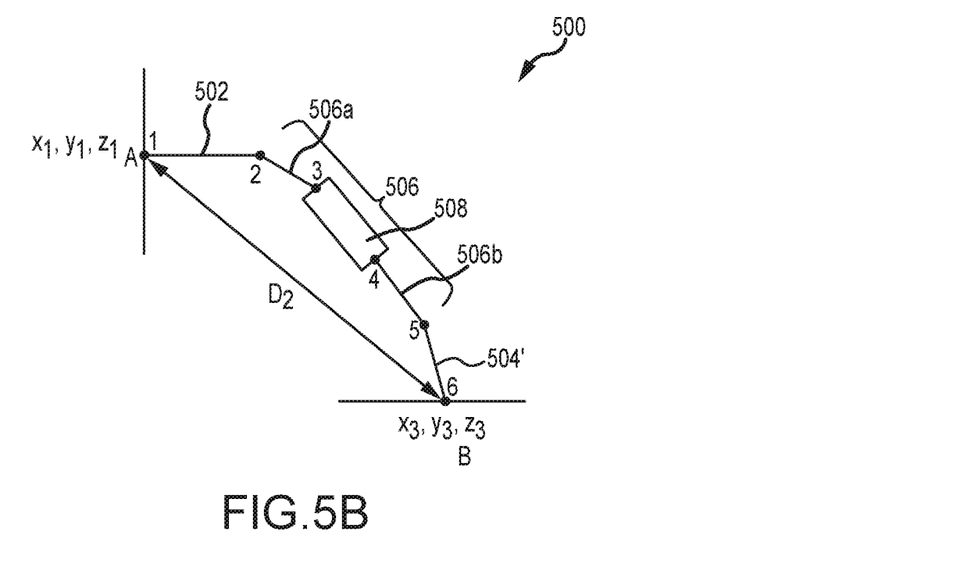
Figure 5C:
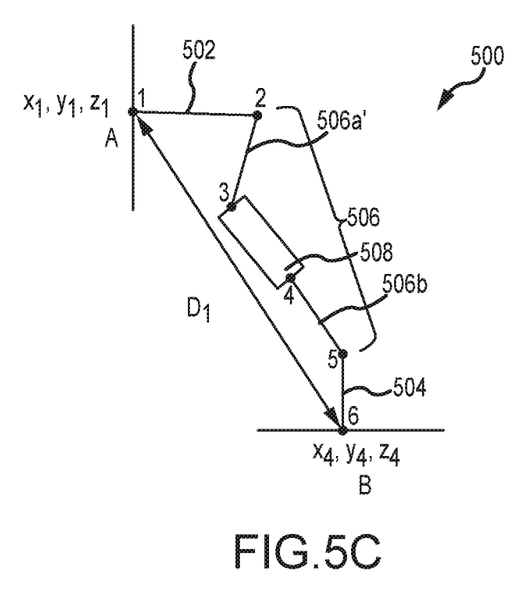

FIGS. 5A-5C depict schematic views of deformable mounting systems 500 for use in direct acoustic stimulators (either cochlear stimulators or middle ear stimulators). Such deformable monitoring systems 500 can be utilized to overcome separation, misalignment, and other problems associated with known direct acoustic stimulator brackets, such as described with regard to FIG. 4. The deformable mounting systems 500 are depicted as basic two-dimensional schematics for clarity, so as to explain the properties thereof. Of course, structure incorporating the disclosed teachings can be three-dimensional. In FIG. 5A, a deformable mounting system 500 includes a fixation element 502, an attachment element 504, and a linkage structure 506. In general, the linkage structure 506 can be any single component, or pluralities thereof, that connect the fixation element 502 to the attachment element 504. The deformable mounting system 500 is fixed at two anchor points A, B, which correspond to two discrete anatomies in a human body. For example, anchor point A can be at the skull, and anchor point B can be at the inner ear or middle ear anatomy. In general, the fixation element 502 and the attachment element 504 are the components of the deformable mounting system closest to their respective anatomies. Anchor point A has a position that can be quantified as $x_1$, $y_1$, $z_1$, while anchor point B has a position that can be quantified as $x_2$, $y_2$, $z_2$. Thus, the two anchor points are separated by a distance D, which can be considered the distance at implantation of a direct acoustic stimulator incorporating the deformable mounting structure 500.

The linkage structure 506 can include a plurality of links or components 506a, 506b, and can also include an actuator element 508, such as the acoustic actuator described herein. In general, the actuator element 508 is the only component of the deformable mounting structure 500 that is not deformable. Joints or connection points between the various components of the deformable mounting structure 500 are depicted as points 1-6. Of course, depending on the number of discrete components in the linkage structure, a greater or fewer number of connection points can be utilized. Notably, when connected to two discrete anatomies, points 1 and 6 can act as anchors. These anchors include but are not limited to, bone screws, bolts, plugs, adhesives, and combinations thereof. Additionally, body structures such as scar tissue, clotted blood, bone or tissue growth, or fluids that display retentive properties, can also act as anchors, although the retention strength associated therewith is fairly low. The points 1-6 can also include rigid or flexible connections, such as joints, hinges, sliding elements, formed interfaces, bolts, screws, adhesives, or combinations thereof. Any of the components 502-506, points 1-6, or portions thereof can be manufactured in whole or in part of a deformable material such as a viscoelastic material so as to accommodate the separation of anchor points A, B, resulting due to bone growth.

FIG. 5B depicts the deformable mounting system 500 of FIG. 5A, where the distance between anchor points A, B has increased to distance $D_2$, which is greater than distance $D_1$. This new distance $D_2$ can be the result of growth of the recipient, and causes the anchor point B to be disposed at a new spatial position characterized by $x_3$, $y_3$, $z_3$. Of course, spatial positions of both anchor points A, B can change, while distance $D_1$ remains the same. In the depicted embodiment, the attachment element 504' is a deformable element and deforms to accommodate distance $D_2$, preventing disconnection of the attachment element 504' from anchor point B or the fixation element 502 from anchor point A.

FIG. 5C depicts the deformable mounting system 500 of FIG. 5A, where the distance between anchor points A, B has maintained distance $D_1$, even though anchor point B being is disposed at a new spatial position characterized by $x_4$, $y_4$, $z_4$. Of course, spatial positions of both anchor points A, B can change while distance $D_1$ remains the same. In the depicted embodiment, the linkage structure portion 506a' is a deformable element and deforms to accommodate the new spatial position of anchor point B, preventing disconnection of the attachment element 504' from anchor point B or the fixation element 502 from anchor point A.

In the embodiments of the deformable mounting system 500 depicted in FIGS. 5A-5C, other components of the deformable mounting system 500 can also be manufactured in whole or in part of a deformable material so as to accommodate relative movement of or separation between anchor points A, B. That is, components between anchor point A and the actuator element 508, as well as components between the actuator element 508 and anchor point B can be manufactured of a deformable material. These components can be in addition to or instead of the single component indicated above as being deformable. Additionally, the above description assumes that the connection of the deformable mounting system 500 is weakest at anchor points A, B. In other embodiments, for example, where connection is made at anchor points A, B with bones screws or other robust connections, the weakest connection can be within the deformable mounting system 500 itself. By utilizing deformable materials in the deformable mounting system 500, failure of the deformable mounting system 500 itself can also be averted.

Figure 6:
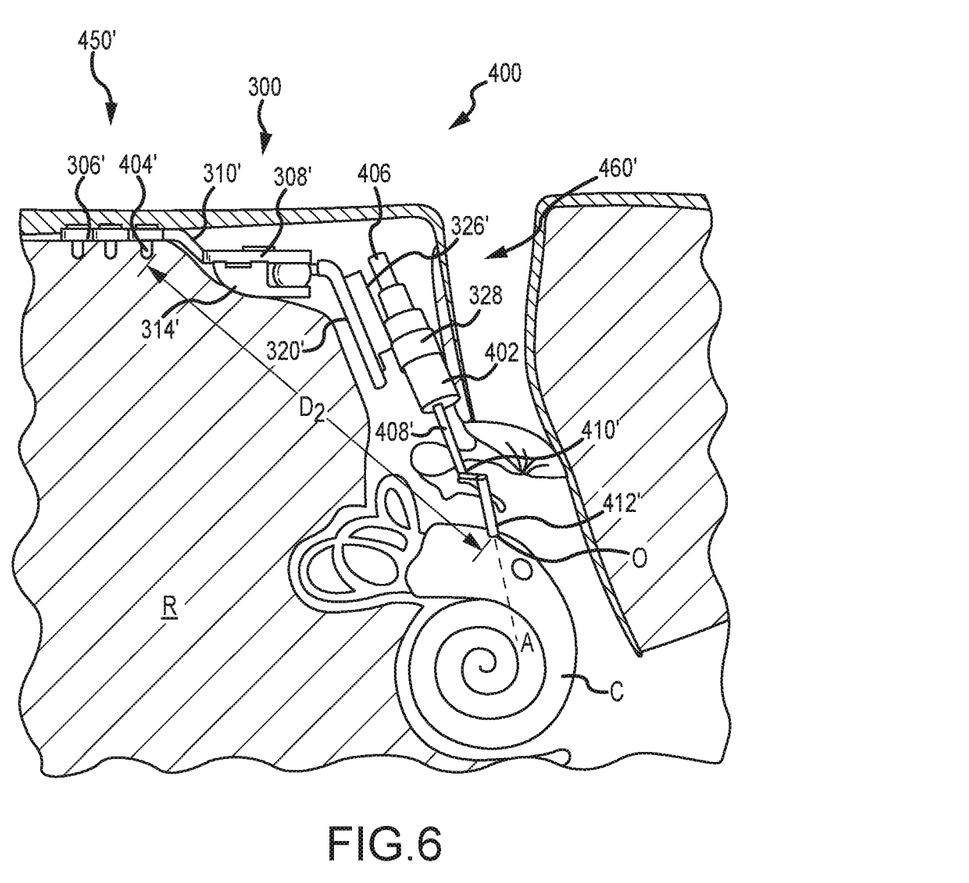
FIG. 6 is a partial view of a direct acoustic stimulator implanted in a recipient.

FIG. 6 is partial view of a direct acoustic stimulator 400 worn on a recipient R in accordance with aspects of the disclosure, as described generally in FIGS. 5A-5C. Certain elements depicted in FIG. 6 are described above in FIGS. 2 and 3 and are not necessarily described further. Deformable elements such as viscoelastic materials can be incorporated into one or more of a fixation element 450', an attachment element 412', or a linkage structure 460'. In fact, any one or more components, e.g., 306', 308', 310', 314', 320', 326', 404', 408', 140', and/or 412' can be manufactured of a viscoelastic material. For example, the fixation element 450' can include a bone plate 306' or securement elements 404' that can be manufactured of a viscoelastic material. The linkage structure 460' can be any of the components that connect the fixation element 405' to the attachment element 412'. In the case of the securement elements 404', specifically, these can be manufactured in the form of rods or shafts of viscoelastic material and adhered or otherwise secured to the skull. As the skull grows and the distance $D_1$ in FIG. 3 increases to the distance $D_2$ of FIG. 6, the viscoelastic material can deform so as to enable the attachment element 412' to remain in contact with the opening O, without the securement elements 404' themselves failing.

The fixation element 450 is connected to a number of components that define a linkage structure 460. Here, the linkage structure 460 includes a transition 310' and a clamp plate 308', either or both of which can be manufactured of a viscoelastic material. In certain aspects, if the clamp plate 308' is manufactured of a viscoelastic material, it can also be advantageous to manufacture the ball clamp 314' of a viscoelastic material so as to provide even deformation. In certain aspects, either or both of the ball plate 320' and the actuator plate 326' can be manufactured of a viscoelastic material. The linkage structure 460 can also include the actuator 402 and a coupling rod 408' moved by the actuator 402 extending therefrom. The linkage structure 460 is connected to an attachment element 412' via a piston 410'. By utilizing a viscoelastic material in any number of the components identified above, growth of the recipient can be accommodated.

Figure 7A:
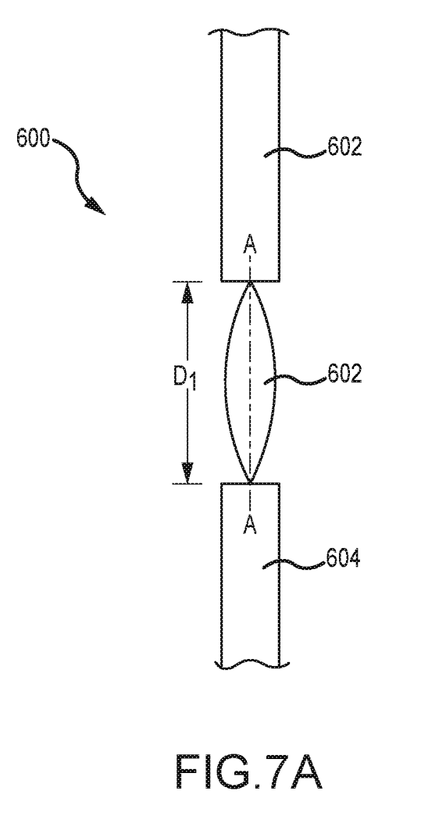
FIGS. 7A and 7B depict schematic side views of a viscoelastic element utilized in deformable mounting system of a direct acoustic stimulator.
Figure 7B:
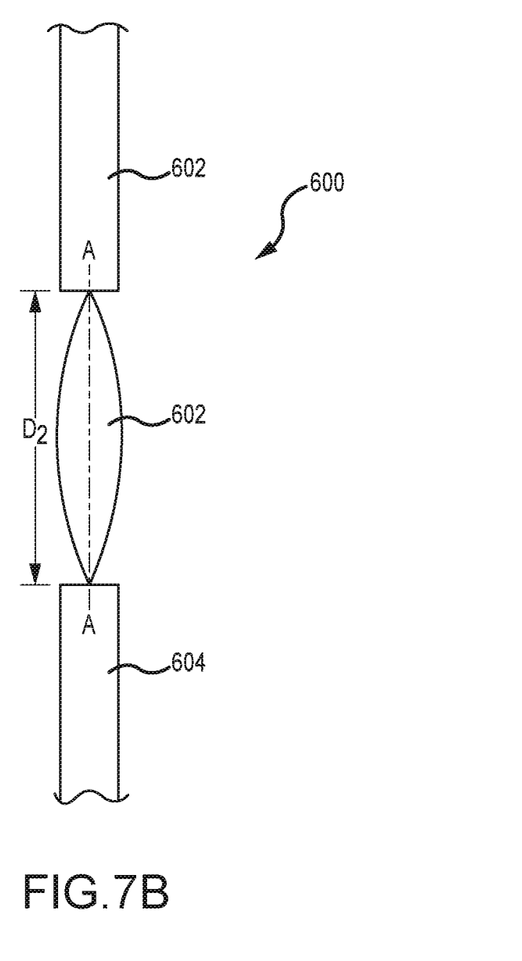

FIGS. 7A and 7B depict schematic side views of a viscoelastic element utilized in a deformable mounting system 600 of a direct acoustic stimulator. The deformable mounting system 600 is depicted in a greatly simplified presentation so as to explain the function of a deformable element or member 602. Here, the deformable element or member 602 is an elongate component of a viscoelastic material and links a first component 604 and a second component 606. In FIG. 7A, the first component 604 and the second component 606 are separated by a first distance $D_1$. The deformable element 602 includes an elongate axis A. As the distance between the first component 604 and the second component 606 increases, e.g., to a second distance $D_2$ depicted in FIG. 7B, the viscoelastic deformable element 602 deforms along its elongate axis A. This deformation allows the connection between the first component 604 and the second component 606 to be maintained. This is analogous with maintaining a connection between two discrete anatomies within a body, while utilizing a deformable mounting system having at least one deformable element.

Figure 8A:
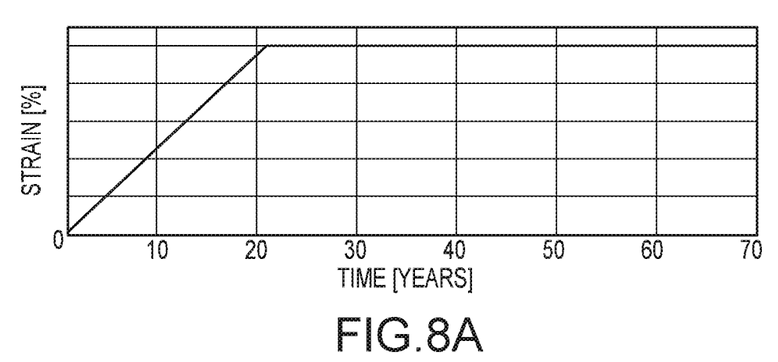
FIGS. 8A and 8B depict plots of stress and strain of a viscoelastic material utilized in a direct acoustic stimulator.
Figure 8B:
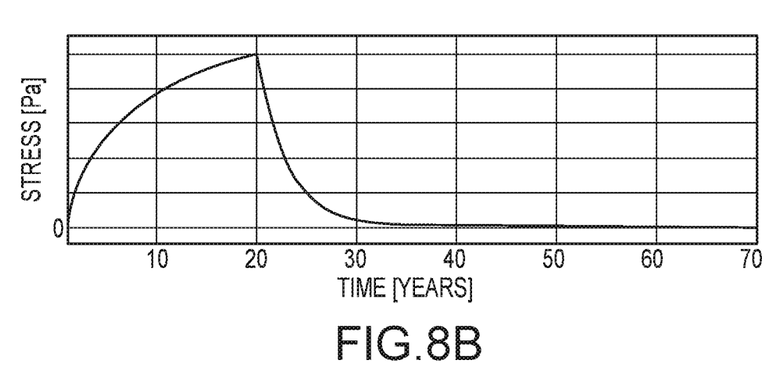

FIGS. 8A and 8B depict plots of stress and strain of a viscoelastic material utilized in a direct acoustic stimulator. The viscoelastic material will yield gradually to decay internal stresses. Thus, when used in the context of an auditory prosthesis, as described herein, as the skull grows, the strain on the device increases linearly, as depicted on the left hand side of FIG. 8A. As a result, the stress in the viscoelastic material will also increase slightly, as depicted on the left hand side of FIG. 8B. However, the stress on a viscoelastic material will not increase as much as a conventional linear elastic material. This is the case because a viscoelastic material relaxes under the presence of strain. In that regard, once the skull is full-grown, the strain no longer increases and instead remains constant, as depicted on the right-hand side of FIG. 8A. As a consequence, the internal stress decays until zero stress remains, as depicted on the right-hand side of FIG. 8B.

This viscoelastic behavior is exhibited at long periods of time or, equivalently, at very low mechanical frequencies. This means that in normal day-to-day activities, a direct acoustic stimulator incorporating a viscoelastic material responds very conventionally to various loads due to inertia. For example, the direct acoustic stimulator will not deform because the recipient is in a car that takes a sharp turn. The viscoelastic material behaves as a high-pass filter. That is, it behaves stiff in response to high frequency mechanical input and dampens very low frequency mechanical input, such as the slow growth of a skull. In that case, the viscoelastic material deforms only due to stresses placed on it due to loads applied over a predetermined length of time. In the described context, this predetermined length of time can be at least one year, and can accommodate anatomical growth during that year. The leniency of viscoelastic material is not exhibited in response to short duration accelerations such as those that are encountered in everyday activities. Everyday activities can result in shocks, inertial forces, vibrations, and impacts being transferred, as is the case with conventional materials. Instead, the viscoelastic material is too slow to adapt to these relative high frequency inputs, due to the material's very high viscosity. In other words, the cutoff frequency of the high-pass filter is too low to respond to such inputs.

By utilizing viscoelastic materials in a direct acoustic stimulator, it is possible to compensate for anatomical changes such as skull growth without surgical interventions later in life. The viscoelastic materials aim for a neutral stress state in the long term, such that the efficiency of the therapy is not affected by bone growth, thus allowing for implantation of such devices in pediatric patients.

This disclosure described some aspects of the present disclosure with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific aspects were described herein, the scope of the technology is not limited to those specific aspects. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An implantable auditory prosthesis, comprising:
   a fixation element configured to be attached to a skull bone of a recipient;
   an attachment element configured to be attached to an internal ear structure of the recipient; and
   a linkage structure connected between the fixation element and the attachment element,
   wherein the linkage structure comprises one or more deformable elements configured to automatically deform, over a period of time, to accommodate a gradual increase in a separation between the skull bone and the internal ear structure of the recipient.

2. The implantable auditory prosthesis of claim 1, wherein the linkage structure comprises an actuator.

3. The implantable auditory prosthesis of claim 2, wherein at least one of the one or more deformable elements is located in a section of the linkage structure coupled between the fixation element and the actuator.

4. The implantable auditory prosthesis of claim 2, wherein at least one of the one or more deformable elements is located in a section of the linkage structure coupled between the actuator and the attachment element.

5. The implantable auditory prosthesis of claim 2, wherein the one or more deformable elements do not comprise the actuator.

6. The implantable auditory prosthesis of claim 1, wherein the attachment element comprises an ossicular chain prosthesis.

7. The implantable auditory prosthesis of claim 1, wherein the attachment element comprises a stapes prosthesis.

8. The implantable auditory prosthesis of claim 1, wherein the fixation element comprises at least one deformable element configured to automatically deform, over the period of time, to accommodate the gradual increase in the separation between the skull bone and the internal ear structure of the recipient.

9. The implantable auditory prosthesis of claim 1, wherein the attachment element comprises at least one deformable element configured to automatically deform, over the period of time, to accommodate the gradual increase in the separation between the skull bone and the internal ear structure of the recipient.

10. The implantable auditory prosthesis of claim 1, wherein the one or more deformable elements each comprise a material configured to gradually yield to decay internal stresses induced by the gradual increase in the separation between the skull bone and the internal ear structure of the recipient.

11. The implantable auditory prosthesis of claim 1, wherein the one or more deformable elements each comprise a material configured to function as a high-pass filter in which the material is stiff in response to high frequency mechanical movement and dampens low frequency mechanical movement induced by the gradual increase in the separation between the skull bone and the internal ear structure of the recipient.

12. The implantable auditory prosthesis of claim 1, wherein the one or more deformable elements each comprise a viscoelastic material having a leniency that is exhibited in response to stresses placed thereon due to loads applied only over the period of time exceeding at least one year.

13. The implantable auditory prosthesis of claim 1, wherein the separation between the skull bone and the internal ear structure of the recipient changes, over the period of time, from a first distance to a second distance, wherein the one or more deformable elements each have a first length at the first distance and a second length at the second distance, and wherein the one or more deformable elements are configured to remain at the second length following the change in the separation between the skull bone and the internal ear structure.

14. A method, comprising:
attaching a fixation element to a skull bone of a recipient;
attaching an attachment element to an internal ear structure of the recipient; and
connecting the fixation element and the attachment element with a linkage structure,
wherein the linkage structure comprises one or more deformable elements configured to automatically deform, over a period of time, to accommodate a gradual increase in a separation between the skull bone and the internal ear structure of the recipient.

15. The method of claim 14, wherein attaching the attachment element to the internal ear structure of the recipient comprises:
attaching the attachment element to an ossicular chain of the recipient.

16. The method of claim 14, wherein attaching the attachment element to the internal ear structure of the recipient comprises:
attaching the attachment element to a stapes of the recipient.

17. The method of claim 14, wherein the linkage structure comprises an actuator.

18. The method of claim 17, wherein at least one of the one or more deformable elements is located in a section of the linkage structure coupled between the fixation element and the actuator.

19. The method of claim 17, wherein at least one of the one or more deformable elements is located in a section of the linkage structure coupled between the actuator and the attachment element.

20. The method of claim 14, wherein the one or more deformable elements comprise a plurality of separate deformable elements located at different locations in the linkage structure.

* * * * *